United States Patent [19]

Smale

[11] Patent Number: 5,597,778
[45] Date of Patent: Jan. 28, 1997

[54] HERBICIDAL COMPOSITIONS CONTAINING DMSO

[76] Inventor: Bernard Smale, 2640 SW. Taibot Rd., Portland, Oreg. 97201

[21] Appl. No.: 475,987

[22] Filed: Jun. 7, 1995

Related U.S. Application Data

[63] Continuation-in-part of Ser. No. 300,267, Sep. 2, 1994, abandoned.

[51] Int. Cl.$^6$ .............................. A01N 57/04; A01N 31/02
[52] U.S. Cl. ........................... 504/127; 504/136; 504/145; 504/206; 504/214; 504/323; 504/324; 504/116; 504/349
[58] Field of Search ................................ 504/116, 127, 504/136, 145, 206, 214, 323, 324

[56] References Cited

U.S. PATENT DOCUMENTS 3,756,801  9/1973  Herschler .................................. 504/116

OTHER PUBLICATIONS

CA: 68: 21097, Mussell et al, "Acceleration of bean leaf abscission . . . ", Can. J. Plant. Sci., 47(6), 635–9, 1967 (abstract only).

Lapham, Virgil T., "Effectiveness of some Dimethylsulfoxide–Herbicide Combinations"—Publication of Aquatic Vegetation Control Research, Wildlife and Fisheries Commission, Baton Rouge, LA. (1966).

*Primary Examiner*—José G. Dees
*Assistant Examiner*—B. Bembenick
*Attorney, Agent, or Firm*—Glenna Hendricks; Stephen Gates

[57] ABSTRACT

The addition of DMSO to herbicidal compositions makes it possible to decrease the amount of active herbicidal agent required for desired activity without loss of effectiveness against target plants. The most preferred compositions for application to the plates contain 1–2.5% DMSO. However, in some instances, it may be advisable to use as much as 3% DMSO. The addition of the DMSO also results in increased stability to the composition.

18 Claims, No Drawings

HERBICIDAL COMPOSITIONS CONTAINING DMSO

This application is a continuation-in-part of U.S. Ser. No. 08/300,267, filed Sep. 2, 1994, now abandoned.

FIELD OF THE INVENTION

This invention is related to means of enhancing effectiveness of herbicides by addition of 1%–2.5% Dimethylsulfoxide (DMSO) to the herbicidal composition whilst reducing the amount of herbicide used. In some instances, especially when the target species has stems or leaves that are particularly impermeable, it may be necessary to increase the amount of DMSO to 3%.

BACKGROUND OF THE INVENTION

The use of herbicides and pesticides has proven to be a mixed blessing to mankind. While the value of increased production of food for human consumption has been important in meeting the nutritional needs of the world, the addition of large amounts of herbicidal substances which are often slowly degraded has caused environmental damage. The regulation of use of herbicides to avoid excess dispersal of these active agents into the environment has become an increasing concern to agriculturalists.

The use of DMSO with herbicides has previously been suggested. A study done in 1964 used DMSO with herbicides in solutions containing 0.5 gpa of DMSO to 1 gpa of a mixture containing picloram-2,4-D mixture. Using this large amount of DMSO proved to result in efficacious killing of plants. However, the cost of such large amounts of DMSO (33%) in herbicidal compositions has not been practiced, and would undoubtedly be too expensive for widespread use. Furthermore, as indicated in this specification, such concentrations are neither necessary nor advisable.

DMSO has also been used in insecticidal compositions. U.S. Pat. No. 3,321,364 discloses use of DMSO with the insecticide for use in compositions containing ryania. The DMSO is in very small amount and appears to be used primarily as a solubilizing agent.

Keil, of the U.S. Department of Agriculture has suggested use of bacteriocidal and fungicidal compositions containing oxytetracycline and 0.25% to 0.5% DMSO. No use of DMSO in herbicidal compositions is taught therein. Keil suggested that the increased effectiveness was apparently due to the increased absorption and translocation of the active agents.

Robert L. Weintraub has studied the effect of DMSO on plants. He found that aqueous solutions containing 40% or greater amounts of DMSO on cacao seedling caused marginal necroses. It was reported that addition of 0.05% to 15% DMSO to various nutritional supplements such as salts, nutrients, metabolites and dyes resulted in increased absorption.

It has also been reported that use of 10% to 100% DMSO as a solvent enhanced penetration of herbicide to leaves. It goes without saying that use of 10% to 100% DMSO would be prohibitively expensive for use in agricultural application.

It was also reported that use of 1% to 5% DMSO in fungicidal compositions resulted in enhancement of action of some fungicides. No improvement in effect was seen when used with some of the fungicides.

DESCRIPTION OF THE INVENTION

It is the purpose of this invention to provide improved post-emergent herbicidal compositions containing greatly reduced amounts of herbicide in formulations containing 0.5 to 2.5% of DMSO. When the target species is particularly impermeable to herbicidal agents, the amount of DMSO in the herbicidal composition may be as high as 3%. A preferred range for DMSO concentration is 1% to 2% DMSO. At the levels of DMSO taught herein, it is possible to avoid damage to the plant absorption process whilst greatly decreasing the amount of herbicide necessary to obtain highly effective response.

The method of the invention may often be practiced by preparing a concentrated composition comprising an herbicide and anhydrous dimethylsulfoxide. Various additives, including detergents, emulsifiers and dispersing agents may be added along with an agriculturally acceptable carrier to provide the desired concentration of active agent for application to plants.

Because DMSO is readily degraded in the natural environment, the addition of DMSO does not present a lingering danger to the ecosystem. The enhancement of the herbicidal activity occasioned by use of DMSO in concentrations taught herein makes it possible to greatly decrease the amount of herbicide that could have more lingering effects when released into the environment. The methods using the preferred amounts disclosed herein will also result in financial savings.

Finally, it is possible to obtain short-term herbicidal effects while decreasing the term of residual soil activity. This reduction is particularly important when using agents such as sulfonylurea herbicides. (CLASSIC™ is an example of such herbicides) Most crops planted in fields previously treated with these herbicides are subject to injury if residual soil activity is present after treatment with these herbicides. The rotational intervals for CLASSIC™ range from 3–15 months, and may be even longer when this herbicide is applied over other herbicides. The major factors contributing to the soil activity are herbicide use rate, soil pH and moisture, air and soil temperature and precipitation. Of these, only the use rate can be readily modified in the field. However, lowering the use rate may limit effectiveness at all time periods following application. By adding DMSO to the carrier as taught herein, it is possible to retain short-term efficacy while lowering the use rate, thus shortening the rotational cycle without loss of short-term efficacy.

It was found that use of about 1% DMSO most frequently resulted in minimal loss of the preferred species of plants while minimizing the amount of active herbicide needed to obtain desired results against the weed population. Use of up to 3% DMSO is acceptable and provides improved effectiveness in a few instances. However, when more that 3% DMSO was present in the compositions, the young crop plants were more likely to be damaged. Moreover, unnecessary cost was incurred by the addition of unnecessarily high levels of DMSO without any increase in benefit. By methods of the invention it has been possible to decrease amount of herbicide in the compositions by 50% to 75% without loss of herbicidal activity.

EXAMPLE 1

Phytotoxicity of DMSO sprays was evaluated on hosta, ferns and azaleas. In each instance, groups of 6 plants were sprayed with 1%, 2%, 5% or 10% aqueous DMSO.

TABLE 1

| Plants | Concentration DMSO | Effects |
| --- | --- | --- |
| hosta | 10% | Margina burn |
| ferns | 10% | burn on fron tips |
| azalea | 10% | non-toxic |
| hosta | 5% | non-toxic |
| ferns | 5% | burn on fron tips |
| azalea | 5% | non-toxic |
| hosta | 2% | non-toxic |
| ferns | 2% | non-toxic |
| azalea | 2% | non-toxic |

At 1% DMSO on all tests, no toxicity was noted.

EXAMPLE 2

A commercial product known as WEED-B-GONE™ containing as active agents 2,4 dichlorophenoxy acetic acid and 2(2-methyl-4-chlorophenoxy) propionic acid was evaluated. The recommended rate of application is 4 teaspoons per gallon. Lower rates of 1 and 2 teaspoons per gallon with DMSO added to provide DMSO concentration of 1%, 0.5% and 0.25% was tested. All plants were sprayed to thoroughly wet the leaves with the following results:

TABLE 2

| Conc. WEED-B-GONE | Conc. DMSO | Plantain | Thistle | Ground Ivy | Curly dock |
| --- | --- | --- | --- | --- | --- |
| 4 tsp/gal | 0 | ++ | ++ | ++ | ++ |
| 2 tsp/gal | 0 | + | ± | ± | ± |
| 1 tsp/gal | 0 | — | — | — | — |
| 4 tsp/gal | 1% | ++++ | ++++ | ++++ | ++++ |
| 2 tsp/gal | 1% | ++++ | ++++ | ++++ | ++++ |
| 1 tsp/gal | 1% | ++ | ++ | ++ | ++ |

Definitions:
— = no effect on plants
+ = slight effect
± = slight to no effect
++ = moderate effect
**** = severe damage to plant Retesting showed similar effects with more

EXAMPLE 3

Glyphosate, the active agent in ROUNDUP™ and other similar non-selective herbicidal products for control of many annual and perennial grasses, broadleaf weeds, woody shrubs and trees was evaluated in greenhouse studies. The $LD_{50}$ range for glyphosate on sickle pod grown in the greenhouse was established at 0.06% and 0.03%. Comparison of percent control of sickle pod by glyphosate with and without DMSO (3%) showed significant improvement in sickle pod control at 0.06% and 0.03% when 3% DMSO was present over control when DMSO was lacking.

Evaluation of effect of the 0.06% glyphosate concentrate over a 30 day interval clearly demonstrated improved early and sustained control of sickle pod with compositions containing 3% DMSO showed increased effectiveness for control of sickle pod at concentration 0.06% and 0.3% in carrier with 3% DMSO. The testing procedure used 12 sickle pod 3 inches high selected for uniformity in each treatment. The rating of injury to each plant was based on visual rating of herbicidal activity with +=10%, ++=25%, +++=50%, ++++ −75% and dead plants =100%

| % herbicide and additive | % control of sickle pod at 12 days |
| --- | --- |
| 0.06% glyphosate only | 51% |
| 0.06% glyphosate with 3% DMSO | 90% |
| 0.03% glyphosate only | 54% |
| 0.03% glyphosate with 3% DMSO | 85% |

Evaluation of the 0.06% glyphosate concentration over a 30 day interval clearly established improved early and sustained control of sickle pod with 3% DMSO compared with control using the glyphosate only.

| | 12 days | 20 days | 30 days |
| --- | --- | --- | --- |
| 0.06% glyphosate only | 51% | 43% | 85% |
| 0.06% glyphosate, 3% DMSO | 90% | 85% | 96% |

EXAMPLE 4

The sulfonylurea herbicides ACCENT™ and CLASSIC™ provide selective weed control of may grasses and broad leaf weeds in crops such as peanuts, alfalfa, soybean, rice, cereal grains and cotton. Use rates of ACCENT™ and CLASSIC™ are low, ranging from ¼ to 1½ ounces per acre.

Green house experiments were conducted demonstrating the sustained efficacy of ACCENT™ and CLASSIC™ at one-half the rate suggested on the label. ACCENT™ label directions for control annual morning glory (2–3 inches height) call for use of ⅔ ounces per acre. CLASSIC™ labels stipulates the same amount for control of annual morning glory and sickle pod. Data show no loss of effectiveness with these active agents when the rate of application was reduced to ⅓ ounce per acre. Increased herbicidal activity with ACCENT™ plus DMSO at 0.66 ounces per acre and 0.33 ounces per acre applications was shown.

| Product and concentration | 9 days | 21 days |
| --- | --- | --- |
| | % control, morning glory | |
| ACCENT ™, 0.66 oz/A | 33% | 52% |
| ACCENT ™ 0.66 oz/A, 2% DMSO | 52% | 67% |
| ACCENT ™ 0.33 oz/A, 2% DMSO | 55% | 65% |
| | % control, sickle pod | |
| CLASSIC ™ 0.66 oz/A | 57.5% | 85% |
| CLASSIC ™ 0.66 oz/A, 2% DMSO | 77.5% | 95% |
| CLASSIC ™ 0.33 oz/A, 2% DMSO | 75% | 90% |
| | % control, morning glory | |
| CLASSIC ™ 0.66 oz/A | 75% | 75% |
| CLASSIC ™ 0.66 oz/A, 2% DMSO | 82.5% | 80% |
| CLASSIC ™ 0.33 oz/A, 2% DMSO | 85% | 92.5% |

Composition of selective and nonselective post emergence herbicides are prepared using 25% to 50% of the recommended amount of the following in carrier containing 1%–2.5% DMSO in the carrier for the suggested herbicides such as atrazine, chlorsulfuron, linuron, chlorimuron ethyl, dalapon, MCPA, diquat, 2,4 D, propanil, alachlor, fluometuron, choramben, fluazifop butyl, amitrole, bentazon, paraquat, diclofop methyl, terbutryn, thiobencarb, sethoxydim, dicamba, pendimethan, and so forth useful for practice of the invention.

EXAMPLE 5

While smaller amounts of DMSO are useful, Glyphosate is most effective when the DMSO content is 2.5% to 3% of the final composition. Based on LD$_{50}$ herbicidal activity range for glyphosate on sickle pod under 6 inches tall, field sprays for control should be prepared as follows: Mix 2.4 quarts anhydrous DMSO, 2 pints ROUNDUP™ and 1.5 pints of TRITON X-100™ to 14 gallons of water in a spray tank with agitator running. Concentrations of DMSO+TRITON X-100™ in finished spray will be 3% and 2% respectively, and concentration of glyphosate will be ½ the recommended rate for 3 inch sickle pod (0.625%). The 20 gallon finish spray is sufficient for on acre.

EXAMPLE 6

Dissolve ACCENT™ 0.33 oz (½ the label rate for control of 1–3 inch morning glory) in 1 quart of anhydrous DMSO. Add with mixing an additional 1 ¾ gallons anhydrous DMSO. Add the DMSO/ACCENT™ concentrate and 1 quart of TRITON X-100™ to 100 gallons of water in a spray tank with agitator running and apply to 1 acre. Concentration in the final product of TRITON X-100™ and DMSO in finished spray are 0.25% and 2% respectively.

EXAMPLE 7

Dissolve CLASSIC™ 0.66 oz (½ the label rate for control of 1–3 inch morning glory) in 1 quart of anhydrous DMSO. Add with mixing an additional 1¾ gallons anhydrous DMSO. add the DMSO/CLASSIC™ concentrate and 1 quart of TRITON X-100™ to 100 gallons of water in a spray tank with agitator running and apply to 1 acre. Concentration in the final product of TRITON X-100™ and DMSO in finished spray are 0.25% and 2% respectively.

EXAMPLE 8

Dissolve ACCENT™ 0.66 oz (½ the label rate for control of 1–3 inch morning glory) in 1 quart of anhydrous DMSO. Add with mixing an additional 1¾ gallons anhydrous DMSO. Add this DMSO/ACCENT™ concentrate and 1 quart of TRITON X-100™ to 100 gallons of water in a spray tank with agitator running and apply to 1 acre. Concentration in the final product of TRITON X-100™ and DMSO in finished spray are 0.25% and 2% respectively.

An added advantage provided by use of DMSO in formulations is that the formulations are more stable than other liquid formulations. At the present time, many herbicides must be formulated from dry products close to the time for application. The concentrates containing DMSO and herbicide showed no change of pH or lowering of activity when tested after two months. The ability to formulate the herbicidal compositions with DMSO for later use eases the preparation of the final composition for use near the site of use.

In making the dilute compositions for administration to the plants, various detergents, emulsifiers and dispersing agents are used. Use of α-[4-(1,1,3,3,-tetramethylbutyl)phenyl]-hydroxy-poly (oxy-1,2,ethyanediyl also known as octoxynol sold as TRITON X-100™ is exemplified. However, other emulsifiers, detergents and dispersing agents known in the art can be used in accord with the teachings of the art. the teachings of the art.

It may also be appropriate to add other pesticides, including insecticides and fungicides, to the compositions of the invention.

I claim:

1. A composition of matter comprising at least one post-emergent herbicide, an agriculturally acceptable carrier and dimethyl sulfoxide wherein the dimethyl sulfoxide accounts for 1% to 2.5% of the total volume of said composition and the post-emergent herbicide is present at a concentration of from 25% to 75% less than the commercially recommended concentration formulation without DMSO.

2. A composition of claim 1 containing a sulfonylurea.

3. A composition of claim 2 containing chlorimuron ethyl.

4. A composition of claim 1 containing 2,4 dichlorophenoxy acetic acid.

5. A composition of claim 1 containing 2(2-methyl-4-chlorophenoxy) propionic acid.

6. A composition of claim 1 containing glyphosate.

7. A composition of matter comprising at least one post-emergent herbicide, an agriculturally acceptable carrier and dimethyl sulfoxide wherein dimethyl sulfoxide accounts for >2.5% to 3% of the total volume of said composition and the post-emergent herbicide is present at a concentration of from 25% to 75% less than the commercially recommended concentration formulation without DMSO.

8. A composition of claim 7 containing a sulfonylurea.

9. A composition of claim 8 containing chlorimuron ethyl.

10. A composition of claim 7 containing 2,4 dichlorophenoxy acetic acid.

11. A composition of claim 7 containing 2(2-methyl-4-chlorophenoxy) propionic acid.

12. A composition of claim 7 containing glyphosate.

13. A method of decreasing the amount of herbicide administered to a crop whilst retaining the full immediate effectiveness against target species consisting essentially of the steps of:

1) adding DMSO to a post-emergent herbicide, 2) adding additional water to provide a concentration of 1%–2.5% DMSO plus an herbicide at a concentration of 25% to 75% less than the commercially recommended concentration formulation without DMSO, and 3) spraying said crop with the composition prepared in step 2.

14. A method of claim 13 wherein, additionally, in step 2, an emulsifier, detergent or dispersing agent is added.

15. A method of decreasing the amount of herbicide administered to a crop whilst retaining the full immediate effectiveness against target species consisting essentially of the steps of:

1) adding DMSO to a post-emergent herbicide, 2) adding additional water to provide a concentration of >2.5% to 3% DMSO plus an herbicide at a concentration of 25% to 75% less commercially recommended concentration formulation without DMSO, and 3) spraying said crop with the preparation prepared in step 2.

16. A method of formulating an post-emergent herbicidal composition comprising the steps of:

1) mixing at least one post-emergent herbicide with dimethylsulfoxide, 2) mixing the composition obtained in step 1 with an emulsifier, detergent or dispersing agent, and 3) diluting the composition obtained in step 2 with an agriculturally acceptable carrier for application to plants.

17. A method of claim 16 wherein the herbicide is glyphosate.

18. A method of claim 16 wherein the dimethyl sulfoxide is anhydrous.

* * * * *